United States Patent [19]

Schwan

[11] 4,002,627
[45] Jan. 11, 1977

[54] 1-BENZYL-3-METHYL-3,4,5,6-TETRAHYDRO-2(1H) PYRIMIDONE

[75] Inventor: Thomas J. Schwan, Norwich, N.Y.

[73] Assignee: Morton-Norwich Products, Inc., Norwich, N.Y.

[22] Filed: Mar. 26, 1976

[21] Appl. No.: 670,651

[52] U.S. Cl. .............................. 260/251 R; 424/251
[51] Int. Cl.² ........................................ C07D 239/04
[58] Field of Search ................................ 260/251 R

[56] References Cited

FOREIGN PATENTS OR APPLICATIONS 1,230,805  12/1962  Germany ........................ 260/251 R
2,110,445  3/1971  Germany ........................ 260/251 R Primary Examiner—Lewis Gotts
Assistant Examiner—D. R. Phillips
Attorney, Agent, or Firm—Anthony J. Franze

[57] ABSTRACT

1-Benzyl-3-methyl-3,4,5,6-tetrahydro-2(1H) pyrimidone possesses pharmacological activity as an antianxiety agent.

1 Claim, No Drawings

1-BENZYL-3-METHYL-3,4,5,6-TETRAHYDRO-2(1H) PYRIMIDONE

This invention relates to chemical compounds. In particular it is concerned with a compound of the formula:

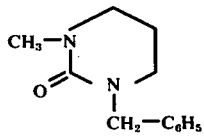

which possesses pharmacological activity affecting the central nervous system. When administered perorally to animals it exhibits antianxiety activity. This antianxiety action is evidenced in the control of pentylenetetrazol induced tonic extensor seizures in mice. An oral dose of 50 mg/kg of this compound to mice intravenously receiving 45 mg/kg of pentylenetetrazol counteracts the effects of pentylenetetrazol.

In order that this invention be readily available to and understood by those skilled in the art, the following example is supplied:

1-Benzyl-3-methyl-3,4,5,6-tetrahydro-2(1H) pyrimidone

To 750 ml toluene stirred at room temperature was added 38 g (0.20 mole) of 1-benzyl-3,4,5,6-tetrahydro-2(1H) pyrimidone. The mixture was stirred at ambient temperatures for 10 min and 14.4 g (0.30 mole) of sodium hydride (50% dispersion in mineral oil) was added at ambient temperature over 5 min. The mixture was stirred at 25° and 60 ml $CH_3I$ was added dropwise over 30 min. The mixture was stirred at ambient temperature for 18 hr, cooled in an ice bath, and 500 ml water was added. The two-phase system was separated and the aqueous layer was extracted with 200 ml toluene. The combined toluene layers were washed with 300 ml $H_2O$, dried ($MgSO_4$), and concentrated to dryness in vacuo. The only residue was stirred vigorously with 150 ml hexane at 0.5° for 90 min to remove mineral oil. The hexane was decanted and the residue was stirred with an additional 150 ml hexane at 0°–5° for 15 min. The hexane was decanted and the residue was washed briefly with another 25 ml hexane. The hexane-insoluble residue was dissolved in $CHCl_3$ and transferred to a distilling flask. Removal of the $CHCl_3$ gave 30.8 g crude oily product.

The product was distilled under reduced pressure at 171°–175° at 1.75 mm Wt. distillate: 21 g (51%).

Anal. Calcd. for $C_{12}H_{16}N_2O$: C, 70.56; H, 7.90; N, 13.72, Found: C, 70.65; H, 7.86; N, 13.76.

What is claimed is:

1. A compound of the formula:

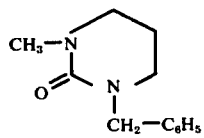

* * * * *